United States Patent [19]

Schumacher

[11] 3,965,220

[45] June 22, 1976

[54] PREPARATION OF ESTERS OF PHOSPHORUS ACIDS

[75] Inventor: Ignatius Schumacher, St. Louis, Mo.

[73] Assignee: Monsanto Company, St. Louis, Mo.

[22] Filed: May 28, 1974

[21] Appl. No.: 473,954

Related U.S. Application Data

[63] Continuation-in-part of Ser. No. 156,561, June 24, 1971, abandoned, which is a continuation-in-part of Ser. No. 103,877, Jan. 4, 1971, abandoned.

[52] U.S. Cl................................. 260/975; 252/46.6; 252/49.8; 252/78; 260/30.6 R; 260/347.3; 260/345.7; 260/930; 260/973
[51] Int. Cl.²...................... C07F 9/08; C07F 9/16; C07F 9/14
[58] Field of Search............................ 260/975, 973

[56] References Cited
UNITED STATES PATENTS

| | | | |
|---|---|---|---|
| 2,033,916 | 3/1936 | Bass | 260/975 X |
| 2,033,918 | 3/1936 | Britton | 260/975 X |
| 2,520,090 | 8/1950 | Burrett | 260/975 X |
| 3,689,602 | 9/1972 | Ismail | 260/975 X |

*Primary Examiner*—Anton H. Sutto
*Attorney, Agent, or Firm*—Robert E. Wexler

[57] ABSTRACT

Esters of phosphorus acids are prepared by an improved process whereby aromatic alcohols and phosphorus halides are reacted at specified temperatures in the presence of amine catalysts thereby providing high yields of substantially pure esters and allowing preparation of selected halogen-containing mono- and di-esters of phosphorus acids wherein halogen is directly bonded to phosphorus having substantially no side reactant contamination. The phosphorus esters are useful as intermediates in the preparation of plasticizers, oil additives and functional fluids.

29 Claims, No Drawings

PREPARATION OF ESTERS OF PHOSPHORUS ACIDS

CROSS REFERENCES TO RELATED APPLICATIONS

This application is a continuation-in-part of copending application Ser. No. 156,561, filed June 24, 1971, now abandoned is, in turn, a continuation-in-part of application Ser. No. 103,877, filed Jan. 4, 1971, now abandoned.

BACKGROUND OF THE INVENTION

This invention relates to a novel process for the preparation of halogen-containing organophosphorus acid esters wherein halogen is directly bonded to phosphorus. More particularly, this invention is concerned with a process comprising an amine catalyzed reaction of halides of phosphorus and hydroxyl-containing organic materials, i.e. aromatic alcohols.

Numerous methods have been long known for preparing triorganphosphorus esters. One of those methods involves the reaction of a phosphoryl halide and a monohydric organic compound without the use of a catalyst. Such a process is not commercially practical because of the need for lengthy reaction times and the resultant low yields. Another disadvantage of processes of that type is the need for the use of excessive amounts of the monohydric organic compound.

Another known method comprises the addition of certain amines to the aforedescribed reaction mixture to effect higher yields. Thus, U.S. Pat. No. 1,785,951 discloses the use of certain aromatic amines, e.g., aniline and pyridine, as catalysts for preparing triaryl phosphates from phosphoryl chloride and a phenol at high temperatures. Similarly, U.S. Pat. No. 2,678,940 discloses the use of aromatic primary amines, e.g., aniline, and certain tertiary alkylamines, e.g., trimethylamine, as catalysts for preparing triaryl phosphites from phosphorus trichloride and a phenol. The cited processes, however, are concerned only with the preparation of triaryl phosphates or phosphites and not with the selective preparation of halogen-containing mono- and di-esters of phosphorus acids.

In still other methods, the reaction is catalyzed, so as to produce greater yields, by adding a metal to the reaction mixture, such as copper powder, iron filings, calcium, aluminum or magnesium; or a halide such as aluminum chloride, magnesium chloride or boron trifluoride; or a sulfate such as copper sulfate; or an oxide such as magnesium oxide or copper oxide.

The employment of such catalysts has several attendant inherent disadvantages, among which are low conversion of the starting materials and lengthly reaction times required for completion of the reaction. As described in U.S. Pat. Nos. 2,610,978 and 2,632,018, an insoluble complex forms during the reaction when aluminum chloride is used as a catalyst.

When alcohols are reacted with a phosphoryl halide, either without a catalyst or in the presence of any of the above-mentioned catalysts, other than magnesium chloride, undesirable by-products are formed. The by-products contribute difficult distillation problems, lower yields of the desired product and lower reaction efficiency. A method described in U.S. Pat. No. 2,410,118 is illustrative of the typical distillation problems encountered. In that method, distillation is difficult due to the high concentration of salts of various phosphorus acids in the distillation still.

U.S. Pat. No. 2,868,827 describes the use of titanium tetrachloride as a catalyst for producing organophosphate esters. Disadvantages encountered employing titanium tetrachloride reside in the excessive and lengthy times necessary to obtain desirable yields and the relatively large amounts of the metal halide catalysts required. Further, when the reaction is conducted in the presence of a titanium halide catalyst, recovery of the desired reaction product is a problem. At the completion of the reaction, it has been found necessary to wash the reaction mixture with a citrate or tartrate solution which forms a complex with the titanium catalyst. The complex is then removed by washing with water followed by drying the remaining product.

Another disadvantage encountered with the employment of many of the aforedescribed catalysts is the need for complicated material-handling procedures for the catalyst.

Additionally, preparation of organophosphorus esters by the aforedescribed catalyzed reactions restricts the manufacturer in that only one specific type of organophosphorus ester of high purity could be prepared by the reaction. Thus, one could not prepare compounds of high purity such as, for example, cresyl phenyl phosphorochloridate, bromophenyl phenyl phosphorochloridate and the like. By the aforedescribed procedures, only relatively impure triorganophosphorus esters or esters containing the same aryl groups could be prepared, for example, triphenyl phosphate, tricresyl phosphate and the like. Thus, in the preparation of organophosphorus esters by the aforedescribed procedures, the specific organophosphorus esters prepared were contaminated by side reactants which could only be removed by lengthy and difficult washing and distillation procedures.

Accordingly, the objective of this invention is to provide a novel and improved process for the preparation of mono- and diorganophosphorus esters in which the disadvantages of the prior art are eliminated and selective esterification in high yields with substantially no by-product contamination is afforded.

SUMMARY OF THE INVENTION

The objective of this invention is accomplished by a novel process, combining a critical combination of catalyst and reaction temperature, for the preparation of halogen-containing organophosphorus acid mono- and di-esters wherein halogen is directly bonded to phosphorus and wherein high yields of product are formed with substantially no side reactions and contaminants and whereby step-wise building of the ester is allowed in such a manner that mixed esters are prepared in an easy and economical manner. As an example of the innovative process of this invention, a compound such as chlorophenyl cresyl phosphorochloridate may be conveniently and inexpensively prepared, such preparation being difficult and expensive with known methods now available to the art. Further, mixtures of mono- and diorganophosphorus esters may be prepared in the same reaction vessel and separated by distillation procedures without undesirable disproportionation.

The unexpected and surprising aspect of the process of this invention is the fact that while the prior art discloses various amines as catalyst for the reaction of, for example, phosphoryl chloride and phenol to prepare triaryl phosphates, it has now been found that not all such amines will catalyze the same type of reaction in the preparation of halogenated mono- and diorganophosphorus esters under the process conditions of this invention. Thus, aniline has been disclosed, among other amine compounds, as a suitable catalyst in the prior art. It has been found, however, that aniline does not function as a catalyst in the process of the present invention, although dimethylaniline is suitable. This difference is believed to be due to a difference in basicity among the amines which is critical in view of the temperatures used in the present process.

The novel process of this invention comprises the preparation of represents and di-esters containing at least one phosphorus-halogen bond by the reaction, at specific temperatures, of halides of phosphorus of the formula

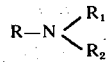  (I)

wherein Y represents R or R'O wherein R represents alkyl, alkenyl, alkynyl, cycloalkyl, cycloalkenyl, cycloalkynyl, heterocyclyl or aryl; R' represents alkyl or aryl; $m$ represents 0 when $n$ is 3 and $m$ represents 1 when $n$ is 2; Z represents a halogen radical, e.g., chloro or bromo; and $n$ represents 2 or 3, with one or two mols of a compound having the formula

R''OH  (II)

wherein R'' represents aryl in the presence of an amine catalyst.

The reaction sequence involved in the process of this invention proceeds through the following stages, exemplified by the reaction of phenol with phosphoryl chloride:

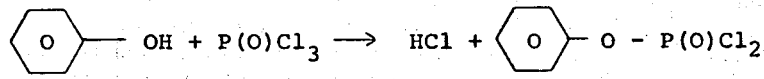

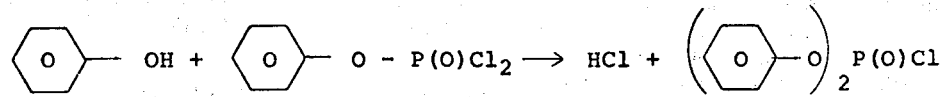

The phosphorus mono- and dihalidates produced are valuable intermediates in the preparation of plasticizers, oil additives and functional fluids and are prepared conveniently by the process of this invention and in high yield with substantially no contamination by side reactions.

The amine catalysts used in the process of this invention may, in general, be any amine which forms a liquid complex with the phosphorus moiety of formula (I) under the conditions of the present process. Essentially all amines which form such a complex are contemplated as catalysts in this process.

The catalyst concentration which is most effective in the process is a function of many variables, but is generally from about 0.001 to 2.0 mole percent based on the phosphorus halide. Preferably, from 0.01 to 0.1 mole percent is considered a practical level. Of course, greater or lesser amounts may be used effectively within the discretion and experience of those skilled in the art. Thus, the following list of amine compounds is intended merely to illustrate the broad scope of the amines which are useful as catalysts herein since it would be virtually impossible to specifically list each amine intended.

Representative amines which may be used as catalysts in the process of this invention include the following compounds, which are illustrative only and are not to be considered a limitation since, as defined above, any amine is suitable providing it complexes with the phosphorus moiety of formula (I) without restriction on the number of carbon atoms in the amine molecule itself and without restriction as to the substituent groups which may be on either the carbon or nitrogen atoms of the amine. By way of illustration, an amine of the formula

can include compounds wherein ont more than two of R, $R_1$ and $R_2$ are hydrogen and wherein R, $R_1$ and $R_2$ each represent alkyl, alkenyl, alkynyl, cycloalkyl, cycloalkenyl, cycloalkynyl, aryl, heterocyclyl or combinations and variations thereof whether substituted or nonsubstituted. Further, R, $R_1$ and $R_2$ may be combined to form a cycloalkyl, cycloalkenyl, cycloalkynyl, heterocyclyl or aryl radical, both substituted and nonsubstituted, and either or both of $R_1$ and $R_2$ may cyclize with R to form an aryl, cycloalkyl, cycloalkenyl, cycloalkynyl or heterocyclyl radical which may be substituted or nonsubstituted. Further, there is virtually no limitation on the number of carbon atoms, or other atoms, in the amine molecule. Accordingly, the only limitation on the size arrangement of the amine used is that or practicality and expense. The following list of illustrative compounds is therefore to be read in the light of the above teachings.

Aliphatic and Alicyclic Amines
methylamine
n-butylamine
tetramethylammonium chloride
neopentylamine hydrochloride
di-n-hexylamine
tridecylamine
diheptylamine
dimethyl-n-butylamine
ditetracontylamine
trioctadecylamine
dihexadecyl eicosylamine
triethylamine
trimethylamine
cyclopropylamine
cyclohexylamine
dicyclohexylamine
1-cyclohexyl-2-aminopropane
tricyclopropylamine
methyl diethylamine
nonyldiundecylamine
isopropylamine
n-amylamine
di-n-butylamine
octadecyl cylcobutylamine
Aromatic Amines
toluidine benzylamine
N-methylaniline
o-phenylethylamine
N,N-dibutylaniline
  N-methyl-alpha-phenetylamine
N-ethyl-toluidine
benzylmethylethylamine
2-naphthylamine
alpha-aminoethylnaphthalene
2-aminobiphenyl
ethyldiphenylamine
1-aminophenanthrene
triphenylamine
methyldibenzylamine
phenanthrylamine
thiophenylamine
chlorophenylamine
nitrophenylamine
butyl cyclohexylamine
dibenzylamine
N,N-dimethylaniline
Heterocyclic Amines
  furfurylamine
  1,3-di-4-piperidylpropane
  ethyleneimine
  pyridine
  2-aminopyridine
  piperidine
  picoline
  2-aminomethylpiperidine
  1-furyl-2-aminopropane
  3-aminothianaphthene quinoline
  1-aminodibenzofuran
  2-aminoacridine
  3-aminodibenzothiophene
  pyridylamine
  pyridoquinolinylamine
  piperidinylamine
  picolinylamine
  benzofuranylamine
  butylpiperidinylamine
  isoamylthienylamine
  dipyridylamine
  cresyl furfurylamine
  imidazole
  1-methylimidazole
Polyamines
  ethylenediamine
  tetramethylenediamine
  hexamethylenediamine
  1-diethylamino-2-aminopropane
  diethylenetriamine
  triethylenetetriamine
  tetraethylenepentamine
  pentamethylenehexamine
  1,2-diaminocyclobutane
  1,4-diaminocyclohexane
  phenylenediamine
  triaminobenzene
  3,3'-diaminobiphenyl
Olefinic Amines
  allylamine
  diallylamine
  triallylamine
  p-aminostyrene
  N-allylaniline
  cis-p-aminostilbene
  ethyl-3-pentenylamine
  octadecyl-6-decenylamine
  decyl cyclohexenylamine
  di-n-propenylamine
  2-propenyl cyclobutylamine
  2-butenyl 3-cyclophenenylamine
  10-octadecenyl phenylamine
  2-butenyl toluidylamine
  cyclohexyl cyclohexenylamine
  dicyclohexenylamine
  2-cyclobutenyl furylamine
Acetylenic Amines
  3-dimethylamine-1-butyne
  5-dibutylamino-3-heptyne
  butyl 3-hexynylamine 6-aminodecyne
  decynyl cyclohexenylamine
Halo Amines
  beta-bromethylamine
  1-amino-2-bromopropane
  1-dimethylamino-3-chlorobutane
  chloroaniline
  fluoroaniline
  chlorobenzylamine
  aminobenzylbromide
  dibromobenzidene
Hydroxy Amines
  3-amino-1-hexanol
  diethylaminomethanol
  3-amino-2-butanol
  5-diethylamino-1-pentanol
  2-aminocyclohexanol
  2-amino-2-cyclopentyl-1-propanol
  aminophenol
  2-anilinoethanol
  3-anilino-1-propanol
  4-amino-1-naphthol
Amino Ketones
  amino acetophenone
  2-phenylamino-3-butanone
  aminobenzophenone It is understood that salts of the contemplated amine catalyst used in the process of this invention are useful and desirable. Thus, the salts of the aforedescribed amines with mineral acids, such as hydrochloric acid and sulfuric acid, and organic acids, such as benzoic and acetic acids, are included within the intended definition of amines as used herein.

Additional illustrative amines which are contemplated as catalysts in the process of this invention are known to those skilled in the art and are set forth at pages 683–714 of Synthetic Organic Chemistry by Wagner and Zook (Wiley and Sons 1953).

The types of phosphorus halides utilized and prepared in accordance with this invention may be either starting materials or intermediates or end products of the process. For instance, a phosphoryl halide may be a starting material used to prepare a dihalidate phosphorus monoester such as a R'-phosphorodihalidate. The R'-phosphorodihalidate may be an intermediate in the preparation of, for example, a monohalidate phosphorus diester such as a di-R'-phosphorohalidate. At the same time, however, the R'-phosphorodihalidate and di-R'-phosphorohalidate may be considered mono- and di-ester end products of the process of this invention. The phosphorus halides utilized are well known to those skilled in the art. Many are commercially available and all are easily prepared in accordance with the process of this invention. Included, ,by way of illustration, are such compounds as:

phosphoryl halides:

R'O phosphorodihalidates:

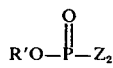

di-R'O phosphorohalidates:

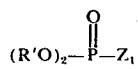

R-phosphonic dihalides:

di-R-phosphinic halides:

R'O-R-phosphonohalidates:

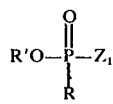

In the above formulas, R, R' and Z are defined as in formula (I).

As described in formula (I), R represents alkyl, e.g., methyl, ethyl, propyl, butyl, amyl, hexyl, heptyl, octyl, decyl, undecyl, dodecyl, pentadecyl, hexadecyl, octadecyl, nonadecyl and eicosyl, whether straight or branched chain in configuration; cycloalkyl, e.g., cyclopropyl, cyclobutyl, cyclopentyl, ethylcyclopropyl, cyclohexyl, methylcyclopentyl, methylcyclohexyl, decahydronaphthyl, bicyclohexyl (cyclohexylcyclohexyl) tetradecahydrophenanthryl, tricyclohexylmethyl; alkenyl, e.g., ethenyl, propenyl, butenyl, isobutenyl, pentenyl, methylbutenyl, trimethylethenyl, hexenyl, heptenyl, octenyl, nonenyl, decenyl, dodecenyl, tridecenyl, hexadecenyl, octadecenyl, eicosenyl; cycloalkenyl, e.g., cyclopropenyl, cyclopentenyl, cyclohexenyl, cyclohexylcyclohexenyl; alkynyl, e.g., ethynyl, propynyl, butynyl, pentynyl, hexynyl, heptynyl, octynyl, nonynyl, decynyl, tridecynyl, octadecynyl, eicosynyl; cycloalkynyl, e.g., 1-cycloden-4-yl; heterocyclic radicals containing oxygen or sulfur in the heterocyclic ring, e.g., thiophenyl, furanyl, tetrahydrofuranyl, pyranyl, sulfolanyl; aryl, e.g., phenyl, naphthyl, biphenyl, phenanthryl, anthracyl, terphenyl or quaterphenyl; and R' represents alkyl or aryl, as described above with reference to R.

R and R' may be unsubstituted, as described above, or substituted. It is to be understood that the amine catalysts of this invention will catalyze the preparation of halogenated organophosphorus esters in accordance with this invention regardless of the type or extent of substitution of the radicals defined as included within R and R' above. Thus the radicals represented by R and R' may be substituted with any moiety except a carboxyl group or a hydroxyl group which may interfere with the reaction.

The following radicals are illustrative of the substituents which may occur on the groups represented by R and R' of the phosphorus halides and R, $R_1$ and $R_2$ of the amine catalysts: alkyl, cycloalkyl, alkenyl, cycloalkenyl, alkynyl, cycloalkynyl, and aryl as described above. Also, halo, e.g., chloro bromo, fluoro, iodo; alkoxy, e.g., methoxy, propoxy, butoxy, hexoxy, decoxy; cycloalkoxy, e.g., cyclohexoxy, cyclobutoxy; alkenoxy, e.g., propenoxy; cycloalkenoxy, e.g., cyclopentenoxy; aryloxy, e.g., phenoxy, naphthoxy; cyano; nitro; isonitro; aldehyde; ketone, alkoxycarbonyl, e.g., methoxycarbonyl; aryloxycarbonyl, e.g., phenoxycarbonyl; alkylcarbonyloxy, e.g., acetyl; alkoxycarbonyloxy, e.g., acetoxy; arlycarbonyloxy, e.g., benzoyl; alkylthio, e.g., ethylthio; arylthio, e.g., phenylthio, napthylthio; trihaloalkyl, e.g., trifluoromethyl; alkylsulfinyl, e.g., butylsulfinyl arylsulfinyl, e.g., phenylsulfinyl; alkylsulfonyl, e.g., propylsulfonyl; arylsulfonyl, e.g., phenylsulfonyl.

Specific phosphorus halides which are encompassed within the scope of this invention, and which may be starting materials and/or desired products, include phosphoryl chloride, phosphoryl bromide, phosphoryl dibromide chloride, phenyl phosphorodichloridate, p-chlorophenyl phosphorodibromidate, p-nitrophenyl phosphorodichloridate, cresyl phosphorodichloridate, o-methoxyphenyl phosphorodichloridate, nonylphenyl phosphorodichloridate, cumylphenyl phosphorodichloridate, o-biphenyl phosphorodichloridate, naphthyl phosphorodichloridate, isopropylphenyl phosphorodichloridate, tert-butylphenyl phosphorodichloridate, isodecyl phosphorodichloridate, diphenyl phosphorochloridate, dicresyl phosphorochloridate, phenylphosphonic dichloride, p-chlorophenylphosphonic dibromide, methylphosphonic dichloride, chloromethylphosphonic dichloride, butyl phosphorodichloridate, hexyl phosphorodichloroidate, octyl phosphorodichloridate, decyl phosporodichloridate, phenyl phenylphosphonochloride, p-nitrophenyl phenylphosphonochloridate, cresyl phenylphosphonochloridate.

The compounds of formulas (I) and (II), described above, are generally known in the art and their methods of preparation are available in standard texts and reference sources.

A preferred class of the compounds of formula (I) are those compounds of the formula

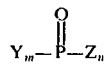

wherein Y = R or R'O wherein R' = aryl or substituted aryl and R, Z, m and n are defined in formula (I). Representative of this preferred class of compounds are phosphoryl chloride, phosphoryl bromide, phenyl phosphorodichloridate, p-chlorophenyl phosphorodibromidate, butyl phosphorodichloridate, hexyl phosphorodichloridate, octyl phosphorodichloridate, decyl phosphorodichloridate, p-nitrophenyl phosphorodichloridate, cresyl phosphorodichloridate, o-methoxyphenylphosphorodichloridate, nonylphenyl phosphorodichloridate, cymyl phenyl phosphorodichloridate, o-biphenyl phosphorodichloridate, naphthyl phosphorodichloridate, isopropylphenyl phosphorodichloridate, tert-butylphenyl phosphorodichloridate, diphenyl phosphorochloridate, dicresyl phosphorochloridate, phenylphosphonic dichloride, p-chlorophenylphosphonic dichloride, methylphosphonic dibromide, chloromethylphosphonic dichloride, phenyl phenylphosphonochloridate, p-nitrophenyl phenylphosphonochloridate, cresyl phenylphosphonochloridate.

The compounds of formula (II) include those compounds wherein R'' represents aryl groups as defined with respect to R and R' of the phosphorus halides. Thus, R'' represents phenyl, alkylphenyl, halophenyl, arylphenyl, cycloalkylphenyl, napthyl, biphenyl, phenanthryl, anthracyl, terphenyl, quaterphenyl.

Specific alcohols of formula (II) are represented by phenol, o, m, p-cresol, o-ethylphenol, o, m, p-isopropylphenol, p-tert-butylphenol, p-tert-amylphenol, nonylphenol, xylenol, o, m, p-chlorophenol, p-bromophenol, p-iodophenol, dichlorophenol, trichlorophenol, pentachlorophenol, p-cumylphenol, o-cylohexylphenol, naphthol, methoxyphenol, ethoxyphenol, phenoxyphenol, nitrophenol, trifuoromethylphenol, allyphenol, benzylphenol, vanillin, 4-chloro-3,5-dimethylphenol, 4-chloro-1-napthol, 2-chloro-4-nitrophenol, cyanophenol, di-tert-butylphenol, dimethoxyphneol, methylsalicylate, flurophenol. Especially preferred of this group are phenol, cresol, cymylphenol, nonylphenol, chlorophenol, tert-butylphenol, xylenol, phenylphenol, isopropylphenol and mixtures thereof.

A specialized class of alcohols which are utilized accordance with this invention are alcohols of the formula

 (III)

wherein R''' represents isopropylidenediphenylene, e.g.,

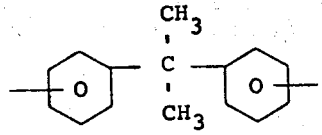

or phenylene, e.g.

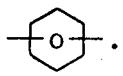

Representative of this special class of alcohols are isopropylidenediphenol, hydroquinone, catechol and resorcinol.

In accordance with the novel process of this invention, the reaction between the phosphorus halides and alcohols to prepare organophosphorus esters proceeds in two stages. Use of the aforedescribed amines, in conjunction with specific temperatures, produces the desired results of this invention. Thus, in the presence of the amine catalysts of this invention, the first chlorine of, for example, phosphoryl chloride is replaced at a temperature of from about 85° to about 135°C., preferably 105°C. The second chlorine, i.e., disubstitution, is replaced at a temperature of from about 130° to about 165°C., preferably 150°C. Of course, the specific temperatures for mono- and di-substitution will vary with the particular reactants being used, but the comparative differences in the temperatures for the stage of substitution will remain approximately the same.

Accordingly, the combination of specific temperatures for mono- and di-substitution of the desired phosphorus halides, together with the catalysts of this invention, enable those skilled in the art to prepare mono- or diorganophosphorus esters in selected proportions. Di-organophosphorus esters may be prepared in two stages, with a different alcohol being added at each stage. Similarly, mixtures of esters may be prepared in one reactor. For example, by adding a naphthyl group at the first stage and a chlorophenyl group at the second stage, one may use the same phosphorus halide but merely introduce different appropriate alcohols at the temperature stages set forth to obtain naphthyl chlorophenyl phosphorochloridate and naphthyl phosphorodichloridate. The different compounds may then be recovered separately by methods known in the art. Further, selected proportions of various compounds may be prepared in the same reactor. Thus, if one desires a mixture of phenyl phosphorodichloridate and naphthyl phenyl phosphorochloridate in proportions of 2:1, such selective proportions of the desired products can be made in accordance with the present invention by adding the intended proportion of each appropriate alcohol in the separate stages.

The following examples will serve to illustrate specific embodiments of the concept of this invention but are not to be regarded as restrictive of the scope thereof since it has been found that the process of this invention promotes the reaction between virtually any phosphorus halide and any alcohol as defined herein.

EXAMPLE 1

To a mixture of 225 g. phosphoryl chloride and 2.6 g. aniline hydrochloride there is added 94 g. phenol over a two-hour period at a temperature of 105°C. The temperature is held at 107°–110°C. for two hours, cooled and stripped of low boilers. Analysis of the residue indicates that it is essentially phenol.

EXAMPLE 2

To a mixture of 225 g. phosphoryl chloride and 1.6 g. N,N-dimethylaniline there is added 94 g. phenol over a two-hour period at a temperature of 100°–106°C. The temperature is held at 105°–110°C. for one and one-half hours, allowed to cool to room temperature and stripped. Distillation affords 73.5 percent phenyl phosphorodichloridate and 4.8 percent diphenyl phosphorochloridate.

EXAMPLE 3

To a mixture of 225 g. phosphoryl chloride and 1.6 g. 1-methylimidazole there is added 94 g. phenol over a two-hour period at a temperature of 105°–107°C. The temperature is held at 105°–110°C. for one hour, cooled and stripped. Distillation affords 198 g. phenyl phosphorodichloridate and 7.4 g. diphenyl phosphorochloridate.

EXAMPLE 4

To a mixture of 225 g. phosphoryl chloride and 2 g. of diethylamine hydrochloride there is added 94 g. phenol over a 2-hour period at a temperature of 105°C. The temperature is then raised to 110°C. and held for two hours, stripped and allowed to cool to room temperature. Dstillation of 212 g. reaction mixture affords 89.9 percent phenyl phosphorodichloridate and 4.5 percent diphenyl phosphorochloridate.

EXAMPLE 5

To a mixture of 225 g. phosphoryl chloride and 1.6 g. pyridine there is added 150 g. p-tert-butylphenol over a period of two hours at a temperature of 100°C. The temperature is then raised to 110°C. and held for two hours, stripped and cooled. Distillation of the reaction mixture affords 94.3 percent p-tert-butylphenyl phosphorodichloridate and 2.5 percent di-p-tert-butylphenyl phosphorochloridate.

EXAMPLE 6

To a reaction vessel there is added 113 g..phosphoryl chloride and 0.8 g. pyridine. Over a period of one hour, a total of 64 g. o-chlorophenol is added and the pot temperature is raised from 100° to 110°C. and held at 110°C. for one hour and then allowed to gradually cool to room temperature. The reaction mixture is stripped and there is obtained 108 g. product which affords, on distillation, 93.7 percent o-chlorophenyl phosphorodichloridate and 7.3 percent di-o-chlorophenyl phosphorochloridate.

EXAMPLE 7

To a mixture of 225 g. phosphoryl chloride and 1.6 g. isoquinoline there is added 94 g. phenol over a 1-hour period at 95°C. The temperature is then raised to 105°C. and held for 2 hours. The reaction mixture is distilled affording 97 percent phenyl phosphorodichloridate and 3 percent diphenyl phosphorochloridate.

EXAMPLE 8

To a reaction vessel there is added 225 g. phosphoryl chloride, 1.6 g. pyridine and 55 g. m-hydroxyphenol and the pot temperature is gradually raised to 115°C. over three hours. Vacuum is applied and distillation of the reaction mixture affords 92.2 percent m-phenylene diphosphorotetrachloridate.

EXAMPLE 9

To a mixture of 113 g. phosphoryl chloride and 0.8 g. pyridine there is added 72 g. alpha-napthol over a one and 1-half hour period at a temperature of 100°C. The temperature is held at 105°–110°C. for one and one-half hours and stripped. Distillation affords 94.6 percent naphthyl phosphorodichloridate and 3.4 percent dinaphthyl phosphorochloridate.

EXAMPLE 10

A mixture of 225 g. phosphoryl chloride, 1.6 g. pyridine and 114 g. 4,4'-isopropylidnendiphenol is heated at 100°–105°C. for 3 hours. The reaction mixture is allowed to cool to room temperature. Distillation affords 4,4'-isopropylidenediphenyl diphosphorotetrachloridate.

EXAMPLE 11

In a reaction pot there is mixed 225 g. phosphoryl chloride and 1.6 g. 2,6-lutidine. Addition of 94 g. phenol is started at a temperature of 95°C. and the total addition is carried out over a period of three hours, during which time the temperature is rasied to 105°C. The reaction is then held at 105°–110°C for an additional one and one-half hours, stripped and cooled. Distillation affords 91.7 percent phenyl phosphorodichloridate and 5.2 percent diphenyl phosphorochloridate.

EXAMPLE 12

To a mixture of 225 g. phosphoryl chloride and 94 g. phenol there is added 1.6 g. quinaldine over a period of 1 hour at 105°C. The temperature is then raised to 105°–110°C. and held for two hours and the reaction mixture is stripped. Distillation affords 76.7 percent phenyl phosphorodichloridate and 4.2 percent diphenyl phosphorochloridate.

EXAMPLE 13

1. To 315 g. phosphoryl chloride and 3.2 g. pyridine there is added 188 g. phenol over a two-hour period at a temperature of 105°C. The temperature is held to 110°C. for 2 hours and allowed to cool. The reaction mixture is principally phenyl phosphorodichloridate.

2. To the reaction mixture of (1), there is added 188 g. phenol and the temperature is raised to 150°C. for 2 hours. The reaction mixture is alllowed to cool and stripped of phenyl phosphorodichloridate. Distillation of the residue affords principally diphenyl phosphorochloridate.

The following table illustrates further examples further examples of the reaction of a phosphorus halide

TABLE

| Example | Phosphorus Halide | Alcohol | Catalyst |
|---|---|---|---|
| 14 | phosphoryl bromide | o, m, p-cresol | triethylamine |
| 15 | phenyl phosphorodichloridate | xylenol | 3-amino-1-pentene |
| 16 | o-methoxyphenyl phosphorodichloridate | nonylphenol | 8-amino-1-nonadecene |
| 17 | chloromethylphosphonic dibromide | o-methoxyphenol | cyclohexylamine |
| 18 | phenyl phosphonodichloridate | 4,4'-isopropylidene diphenol | furfurylamine |
| 19 | p-chlorophenyl phosphorodibromidate | p-cumylphenol | naphthylamine |
| 20 | cresyl phosphorodichloridate | p-tert-amylphenol | tribenzylamine |
| 21 | nonylphenyl phosphorodichloridate | pentachlorophenol | imidazole |
| 22 | cumylphenyl phosphorodibromidate | phenoxyphenol | ethylenediamine |
| 23 | naphthyl phosphorodichloridate | p-bromophenol | p-phenylenediamine |
| 24 | phenylphosphonic dichloride | nitrophenol | diallylamine |
| 25 | cumyl phosphorodichloridate | nonylphenol | chloroaniline |
| 26 | phenyl phosphorodichloridate | fluorophenol | aminobenzophenone | and an aromatic alcohol in the presence of an amine catalyst.

EXAMPLE 27

1. To a mixture of 225 g. phosphoryl chloride and 1.6 g. 1-methylimidazole there is added 109 g. cresol over a period of 2 hours at a temperature of 105°C. The temperature is held at 105°–110°C. for two hours to afford cresyl phosphorodichloridate.

2. The temperature of the reaction mixture obtained in (1) is raised to 135°C. and 109 g. cresol is fed into the reactor over a two hour period. The temperature is held at 150°C. for an additional one and one-half hours to afford dicresyl phosphorochloridate.

EXAMPLE 28

1. To a mixture of 225 g. phosphoryl chloride and 2 g. diethylamine hydrochloride there is added 94 g. phenol over a two-hour period at a temperature of 105°–110°C. The temperature is held for two hours at 110°–115°C. to afford phenyl phosphorodichloridate.

2. The temperature of the reaction mixture of (1) is raised to 135°C. and 109 g. cresol is fed into the reactor during 2 hours. The temperature is held at 150°C. for an additional two hours to afford cresyl phenyl phosphorochloridate.

EXAMPLE 29

1. To a mixture of 920 g. phosphoryl chloride and 1.5 g. methylamine there is added a mixture of 614 g. cumylphenol and 794 g. nonylphenol during 2 hours at a temperature of 105°–110°C. to afford a mixture of cumylphenyl phosphorodichloridate and nonylphenyl phosphorodichloridate.

2. The temperature of the reaction mixture obtained in (1) is raised to 135°C. and 564 g. phenol is added over a 2 hour period. The temperature is held at 150°C. for an additional one and one-half hours to afford a mixture of cumylphenyl phenyl phosphorochloridate and nonylphenyl phenyl phosphorochloridate.

EXAMPLE 30

1. To a mixture of 225 g. phosphoryl chloride and methylamine there is added 109 g. cresol over a period of 2 hours at a temperature of 105°C. The temperature is held at 105°–110°C. for two hours to afford cresyl phosphorodichloridate.

2. The temperature of the reaction mixture obtained in (1) is raised to 135°C. and 94 g. phenol is added during 2 hours at a temperature of 150°C. and held for an additional 2 hours to afford cresyl phenyl phosphorochloridate.

The embodiment of the invention in which an exclusive property or privilege is claimed are defined as follows:

1. The process of preparing a mono- or di-ester of a phosphorus acid containing at least one phosphorus-halogen bond which comprises reacting a phosphorus halide of the formula

wherein
Y represents R or R'O;
R represents alkyl, alkenyl, alkynyl, cycloalkyl cycloalkenyl, cycloalkynyl, heterocyclyl or aryl;
R' represents alkyl or aryl;
$m$ represents 0 when n=3 and 1 when n=2;
$n$ represents 2 or 3; and
Z represents chloro or bromo with a compound of the formula

R"OH wherein
R" represents aryl at a temperature of from about 85°C. to about 165°C. in the presence of a catalytic amount of pyridine.

2. The process of claim 1 wherein R" is selected from the group consisting of phenyl, cresyl, cumylphenyl, nonylphenyl, xylyl, tert-butylphenyl, phenylyl, isopropylphenyl, chlorophenyl and mixtures thereof.

3. A process for preparing an organophosphorus dihalidate which comprises reacting a phosphorus halide according to claim 1 wherein n=3 with an approximately one molar amount of a compound of the formula R"OH according to claim 1 at a temperature of from about 85°C. to about 135°C. in the presence of a catalytic amount of pyridine or an alkyl-substituted pyridine.

4. The process of claim 3 wherein R" is selected from phenyl, cresyl, cumylphenyl, nonylphenyl, xylyl, tert-butylphenyl, phenylyl, isopropylphenyl, chlorophenyl and mixtures.

5. The process of claim 3 wherein said organophosphorusdihalidate is selected from phenyl phosphordichloridate, phenylyl phosphorodichloridate, cresyl phosphorodichloridate, tert-butylphenyl phosphorodichloridate, cumylphenyl phosphorodichloridate, nonylphenyl phosphorodichloridate, xylyl phosphorodichloridate, isopropylphenyl phosphorodichloridate, chlorophenyl phosphorodichloridate and mixtures thereof.

6. A process for preparing a diorganophosphorus halidate which comprises reacting an organophosphorus dihalidate with an approximately one molar amount of a compound of the formula R"OH according to claim 1 at a temperature of from about 130°C. to about 165°C. in the presence of a catalytic amount of pyridine.

7. The process of claim 6 wherein said diorganophosphorus halidate is selected from nonylphenyl phenyl phosphorochloridate and cumylphenyl phenyl phosphorochloridate and mixtures thereof.

8. A process for preparing organophosphorus esters containing at least one phosphorus-halogen bond which comprises reacting, in the presence of a catalytic amount of pyridine, (1) a phosphorus halide of claim 1 with an approximately one molar amount of a first compound of the formula R"OH of claim 1 at a temperature of about 85°–135°C. to form an organophosphorusdihalidate and (2) adding an approximately one molar amount of a second compound of formula R"OH of claim 1 to the reaction product of (1) at a temperature of about 130°–165°C. to form a diorganophosphorushalidate.

9. The process of claim 8 wherein said compouund of formula R"OH is selected from phenol, cresol, cumylphenol, nonylphenol, xylenol, tert-butylphenol, phenylphenol, isopropylphenol, chlorophenol and mixtures thereof.

10. The process of preparing an organophosphorus ester containing at least one phosphorus-halogen bond which comprises reacting a phosphorus halide of the formula

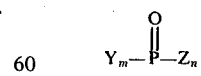

wherein
Y represents R or R'O;
R represents alkyl, alkenyl, alkynyl, cycloalkyl, cycloalkenyl, cycloalkynyl, heterocyclyl or aryl;
R' represents aryl;
$m$ represents O when n=3 and 1 when n=2;
$n$ represents 2 or 3; and Z represents chloro or bromo with a compound of the formula

HO - R'''- OH wherein
R''' represents isopropylidenediphenylene or phenylene at a temperature of from about 85°C. to about 165°C. in the presence of a catalytic amount of pyridine.

11. The process of preparing a mono- or di-ester of a phosphorus acid containing at least one phosphorus-halogen bond which comprises reaction phosphoryl chloride with phenol at a temperature of from about 85°C. to about 165°C. in the presence of a catalytic amount of pyridine.

12. The process of preparing a mono- or di-ester of a phosphorus acid containing at least one phosphorus-halogen bond which comprises reacting a phosphorus halide of the formula

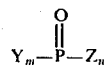

wherein
Y represents R or R'O;
R represents alkyl, alkenyl, alkynyl, cycloalkyl, cycloalkenyl, cycloalkynyl, heterocyclyl or aryl;
R' represents alkyl or aryl;
$m$ represents 0 when n=3 and 1 when $n$=2;
$n$ represents 2 or 3; and
Z represents chloro or bromo with a compound of the formula

R'OH wherein
R'' represents aryl at a temperature of from about 85°C. to about 165°C. in the presence of a catalytic amount of isoquinoline.

13. A process for preparing an organophosphorus dihalidate which comprises reacting a phosphorus halide according to Claim 12 wherein $n$=3 with an approximately one molar amount of a compound of the formula R''OH according to claim 12 at a temperature of from about 85°C. to about 135°C. in the presence of a catalytic amount of isoquinoline.

14. A process for preparing a diorganophosphorus halidate which comprises reacting an organophosphorus dihalidate with an approximately one molar amount of a compound of the formula R''OH according to claim 12 at a temperature of from about 130°C. to about 165°C. in the presence of a catalytic amount of isoquinoline.

15. A process for preparing organophosphorus esters containing at least one phosphorus-halogen bond which comprises reacting, in the presence of a catalytic amount of isoquinoline, (1) a phorphorus halide of claim 12 with an approximately one molar amount of a first compound of the formula R''OH of claim 12 at a temperature of about 85°–135°C. to form an organophosphorushalidate and (2) adding an approximately one molar amount of a second compound of formula R''OH of Claim 12 to the reaction product of (1) at a temperature of about 130°–165°C. to form a diorganophosphorushalidate.

16. The process of preparing an organophosphorus ester containing at least one phosphorus-halogen bond which comprises reacting a phosphorus halide of the formula

wherein
Y represents R or R'O;
R represents alkyl, alkenyl, alkynyl, cycloalkyl, cycloalkenyl, cycloalkynyl, heterocyclyl or aryl;
R' represents aryl;
$m$ represents 0 when $n$=3 and 1 when $n$=2;
$n$ represents 2 or 3; and
Z represents chloro or bromo with a compound of the formula

HO - R''' - OH wherein
R''' represents isopropylidenediphenylene or phenylene at a temperature of from about 85°C. to about 165°C. in the presence of a catalytic amount of isoquinoline.

17. The process of preparing a mono- or di-ester of a phosphorus acid containing at least one phosphorus-halogen bond which comprises reacting phosphoryl chloride with phenol at a temperature of from about 85°C. to about 165°C. in the presence of a catalytic amount of isoquinoline.

18. The process of preparing a mono- or di-ester of a phosphorus acid containing at least one phosphorus-haogen bond which comprises reacting a phosphorus halide of the formula

wherein
Y represents R or R'0;
R represents alkyl, alkenyl, alkynyl, cycloalkyl, cycloalkenyl, cycloalkynyl, heterocyclyl or aryl;
R' represents alkyl or aryl;
$m$ represents 0 when $n$=3 and 1 when $n$=2;
$n$ represents 2 or 3; and
Z represents chloro or bromo
with a compound of the formula

R''OH wherein
R'' represents aryl at a temperature of from about 85°C. to about 165°C. in the presence of a catalytic amount of lutidine.

19. A process for preparing an organophosphorus dihalidate which comprises reacting a phosphorus halide according to Claim 18 wherein n=3 with an approximately one molar amount of a compound of the formula R''OH according to Claim 18 at a temperature of from about 85°C. to about 135°C. in the presence of a catalytic amount of lutidine.

20. A process for preparing a diorganophosphorus halidate which comprises reacting an organophosphorus dihalidate with an approximately one molar amount of a compound of the formula R''OH according to Claim 18 at a temperature of from about 130°C. to about 165°C. in the presence of a catalytic amount of lutidine.

21. A process for preparing organophosphorus esters containing at least one phosphorus-halogen bond which comprises reacting, in the presence of a catalytic amount of lutidine, (1) a phosphorus halide of Claim 18 with an approximately one molar amount of a first compound of the formula R"OH of Claim 18 at a temperature of about 85°–135°C. to form an organophosphorusdihalidate and (2) adding an approximately one molar amount of a second compound of formula R"OH of Claim 18 to the reaction product of (1) at a temperature of about 130°–165°C. to form a diorganophosphorushalidate.

22. The process of preparing an organophosphorus ester containing at least one phosphorus-halogen bond which comprises reacting a phosphorus halide of the formula

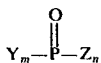

wherein
Y represents R or R'0;
R represents alkyl, alkenyl, alkynyl, cycloalkyl, cycloalkenyl, cycloalkynyl, heterocyclyl or aryl;
R' represents aryl;
m represents 0 when n=3 and 1 when n=2;
n represents 2 or 3; and
Z represents chloro or bromo with a compound of the formula

HO - R''' - OH wherein
R''' represents isopropylidenediphenylene or phenylene at a temperature of from about 85°C. to about 165°C. in the presence of a catalytic amount of lutidine.

23. The process of preparing a mono- or di-ester of a phosphorus acid containing at least one phosphorus-halogen bond which comprises reacting phosphoryl chloride with phenol at a temperature of from about 85°C. to about 165°C. in the presence of a catalytic amount of lutidine.

24. The process of preparing a mono- or di-ester of a phosphorus acid containing at least one phosphorus-halogen bond which comprises reacting a phosphorus halide of the formula

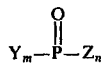

wherein
Y represents R or R'0;
R represents alkyl, alkenyl, alkynyl, cycloalkyl, cycloalkenyl, cycloalkynyl, heterocyclyl or aryl;
R' represents alkyl or aryl;
m represents 0 when n=3 and 1 when n=2;
n represents 2 or 3; and
Z represents chloro or bromo with a compound of the formula

R"OH wherein
R" represents aryl at a temperature of from about 85°C. to about 165°C. in the presence of a catalytic amount of triethylamine.

25. A process for preparing an organophosphorus dihalidate which comprises reacting a phosphorus halide according to Claim 24 wherein n=3 with an approximately one molar amount of a compound of the formula R"OH according to Claim 24 at a temperature of from about 85°C. to about 135°C. in the presence of a catalytic amount of triethylamine.

26. A process for preparing a diorganophosphorus halidate which comprises reacting an organophosphorus dihalidate with an approximately one molar amount of a compound of the formula R"OH according to Claim 24 at a temperature of from about 130°C. to about 165°C. in the presence of a catalytic amount of triethylamine.

27. A process for preparing organophosphorus esters containing at least one phosphorus-halogen bond which comprises reacting, in the presence of a catalytic amount of triethylamine, (1) a phosphorus halide of Claim 24 with an approximately one molar amount of a first compound of the formula R"OH of claim 24 at a temperature of about 85°–135°C. to form an organophosphorusdihalidate and (2) adding an approximately one molar amount of a second compound of formula R"OH of claim 24 to the reaction product of (1) at a temperature of about 130°–165°C. to form a diorganophosphorushalidate.

28. The process of preparing an organophosphorus ester containing at least one phosphorus-halogen bond which comprises reacting a phosphorus halide of the formula

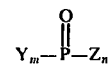

wherein
Y represents R or R'0;
R represents alkyl, alkenyl, alkynyl, cycloalkyl, cycloalkenyl, cycloalkynyl, heterocyclyl or aryl;
R' represents aryl;
m represents 0 when n=3 and 1 when n=2;
n represents 2 or 3; and
Z represents chloro or bromo
with a compound of the formula

HO - R''' - OH wherein
R''' represents isopropylidenediphenylene or phenylene at a temperature of from about 85°C. to about 165°C. in the presence of a cataltyic amount of triethylamine.

29. The proccess of preparing a mono- or di-ester of a phosphorus acid containing at least one phosphorus-halogen bond which comprises reacting phosphoryl chloride with phenol at a temperature of from about 85°C. to about 165°C. in the presence of a catalytic amount of triethylamine.

* * * * *

UNITED STATES PATENT OFFICE
CERTIFICATE OF CORRECTION

PATENT NO. : 3,965,220
DATED : June 22, 1976
INVENTOR(S) : Ignatius Schumacher

It is certified that error appears in the above-identified patent and that said Letters Patent are hereby corrected as shown below:

Column 5, line 6 after "ethyl-" there should be added -- m- --.

Column 6, line 17, "bromethylamine" should be corrected to read -- bromoethylamine --.

Column 14, line 9 (Claim 3) "or an alkyl-substituted pyridine" should be deleted.

Column 14, line 14 (Claim 4) after "mixtures" there should be added -- thereof --.

Column 15, line 13 (Claim 11) "reaction" should be corrected to read -- reacting --.

Column 15, line 36 (Claim 12) the formula "R'OH" should be corrected to read -- R"OH --.

Signed and Sealed this

Twelfth Day of October 1976

[SEAL]

Attest:

RUTH C. MASON
Attesting Officer

C. MARSHALL DANN
Commissioner of Patents and Trademarks